(12) United States Patent
Hagiya et al.

(10) Patent No.: US 6,489,505 B2
(45) Date of Patent: Dec. 3, 2002

(54) PROCESS FOR PRODUCING 3,3-DIMETHYL-2-FORMYLCYCLOPROPANE-CARBOXYLIC ACID ESTER

(75) Inventors: Koji Hagiya, Takatsuki (JP); Ichiro Komoto, Tokyo (JP); Akio Kurihara, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/769,290

(22) Filed: Jan. 26, 2001

(65) Prior Publication Data

US 2002/0010361 A1 Jan. 24, 2002

(30) Foreign Application Priority Data

Jan. 28, 2000 (JP) .......................... 2000-019971

(51) Int. Cl.[7] .................... C07C 69/66; C07C 69/72
(52) U.S. Cl. ............... 560/174; 560/177; 560/178
(58) Field of Search ................ 560/174, 177, 560/178

(56) References Cited

U.S. PATENT DOCUMENTS

| | | | | |
|---|---|---|---|---|
| H49 | H | 4/1986 | Levenberg | .............. 560/124 |
| 3,723,469 | A | 3/1973 | Martel | .............. 260/343.3 |
| 4,014,918 | A | 3/1977 | Martel | .............. 260/468 |
| 6,303,828 | B1 * | 10/2001 | Fischer et al. | |

FOREIGN PATENT DOCUMENTS

| | | | |
|---|---|---|---|
| CN | 1044454 | 8/1990 | |
| JP | 57095921 | 6/1982 | |
| JP | 61289051 | 12/1986 | |
| JP | 6219548 | * 1/1987 | ........... C07C/47/02 |
| JP | 62-19548 | * 1/1987 | |
| JP | 62019548 | 1/1987 | |
| JP | 62029546 | 2/1987 | |
| JP | 6346732 B | 9/1988 | |
| JP | 6356207 B2 | 11/1988 | |
| JP | 684324 B2 | 10/1994 | |
| JP | 699355 B2 | 12/1994 | |
| JP | 819027 B2 | 2/1996 | |
| WO | WO 9500243 | 1/1995 | |
| WO | WO9847847 A1 | 10/1998 | |
| WO | WO 98/47847 | * 10/1998 | |

OTHER PUBLICATIONS

Crombie et al, J. Chem. Soc. Perkin Trans. I, 1980, pp. 1711–1717.*
L. Crombie et al., J. Chem. Soc., Perkin Tran 1, 1980, pp. 1711–1717.
Deng Jingfa et al., Tetrahedron, vol. 48, No. 17, pp. 3503–3514, 1992.
Hiroshi Furukawa et al., Chemistry Letters, pp. 877–880, 1988.

* cited by examiner

Primary Examiner—Alan L. Rotman
Assistant Examiner—Hector M. Reyes
(74) Attorney, Agent, or Firm—Birch, Stewart, Kolasch & Birch, LLP

(57) ABSTRACT

There is provided a process for producing 3,3-dimethyl-2-formylcyclopropanecarboxylic ester of formula (1):

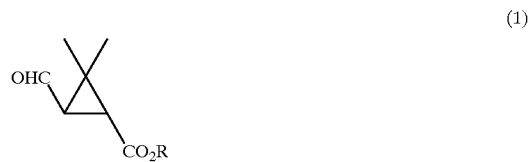

(1)

wherein R represents an alkyl group, a cycloalkyl group or an optionally substituted aralkyl group, which comprises reacting chrysanthemic acid ester of formula (2):

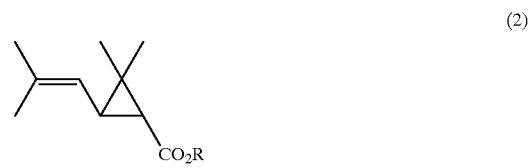

(2)

wherein R represents the same meaning as that described above, with hydrogen peroxide in the presence of at least one catalyst selected from tungstic oxide, tungstic acid, tugstate, alkylrhenium trioxide, molybdic oxide, molybdate, a heteropoly acid comprising a hetero atom selected from a phosphorus, boron or silicone atom and a poly atom selected from tungsten or molybdenum and a salt of said heteropoly acid.

3 Claims, No Drawings

PROCESS FOR PRODUCING 3,3-DIMETHYL-2-FORMYLCYCLOPROPANE-CARBOXYLIC ACID ESTER

FIELD OF THE INVENTION

The present invention relates to a process for producing 3,3-dimethyl-2-formylcyclopropane-carboxylic acid ester.

BACKGROUND OF THE INVENTION 3,3-dimethyl-2-formylcyclopropanecarboxylic acid ester has been known as an intermediate compound of insecticidally effective chrysanthemic acid ester derivatives.

As a process for producing 3,3-dimethyl-2-formylcyclopropanecarboxylic ester, for example, there have been known a method of ozone-oxidizing of chrysanthemic acid (for example, GP-B 46-24695), a method of using periodic acid (US-H49) and the like. However, these methods have been not always satisfactory in that the former method has a problem of handling of ozone having a strong toxicity and explosive property, and the latter has a problem in that expensive periodic acid is required.

SUMMARY OF THE INVENTION

According to the present invention, 3,3-dimethyl-2-formylcyclopropanecarboxylic esters can be readily produced by using hydrogen peroxide and the catalyst below.

The present invention provides:

a process for producing 3,3-dimethyl-2-formylcyclopropanecarboxylic acid ester of formula (1):

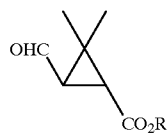

(1)

wherein R represents an alkyl group, a cycloalkyl group or an optionally substituted aralkyl group,
which comprises reacting 3,3-dimethyl-2-(2-methyl-1-propenyl)-cyclopropanecarboxylic acid ester of formula (2):

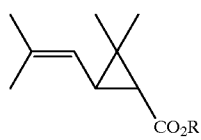

(2)

wherein R represents the same meaning as defined above, with hydrogen peroxide in the presence of at least one catalyst selected from tungstic oxide, tungstic acid, tugstate, alkylrhenium oxide, molybdic oxide, molybdate, a heteropoly acid comprising a hetero atom selected from a phosphorus, boron or silicone atom and a poly atom selected from tungsten or molybdenum and a salt of said heteropoly acid.

DETAILED DESCRIPTION

First, a description will be made to the 3,3-dimethyl-2-(2-methyl-1-propenyl)-cyclopropanecarboxylic acid ester, (chrysanthemic acid ester) of formula (2) as defined above.

Chrysanthemic acid theoretically has (+)-isomer and (−)-isomer resulting from stereochemical configuration around the asymmetric carbon atom connected with the carboxyl group and said isomers have a cis-isomer and a trans-isomer relating to the relative configuration of said carboxyl group and the propenyl group connected with the carbon atom adjacent to the said asymmetric carbon atom in the cyclopropane ring. In the present process, a chrysanthemic acid ester containing said (+)-isomer and (−)-isomer in an optional ratio or respective isomer alone can be used without affecting the stereochemistry of the product. For example, (+)-trans isomer, (−)-trans-isomer, (+)-cis isomer, or (−)-cis isomer of the above described chrysanthemic acid esters and an optional mixture thereof can be used in the present process.

Examples of the alkyl group represented by R in formulae (1) and (2) include a linear or branched lower alkyl group having 1–5 carbon atoms. Specific examples thereof include a methyl group, an ethyl group, a n-propyl group, an isopropyl group, a n-butyl group, an isobutyl group, a sec-butyl group, a tert-butyl group, a n-pentyl group and the like.

Examples of the cycloalkyl group represented by R in formulae (1) and (2) include a cycloalkyl group having 3–10 carbon atoms. Specific examples thereof include a cyclopropyl,group, a cyclobutyl group, a cyclopentyl group, a cyclohexyl group, a menthyl group and the like.

Examples of the optionally substituted aralkyl group include a phenyl- or naphthyl-substituted (C1–C5)alkyl group, of which phenyl group or naphthyl group may be substituted with at least one group selected from the linear or branched lower alkyl group having 1–5 carbon atoms as described above, a lower alkoxy group having 1–5 carbon atoms, a halogen atom, a haloalkyl group having 1–5 carbon atoms, a phenoxy group, and an alkoxyalkyl group having 2–4 carbon atoms.

Preferred phenyl- or naphthyl-substituted alkyl group is a benzyl group.

Examples of the lower alkoxy group having 1–5 carbon atoms include a methoxy, ethoxy, isopropoxy, n-propoxy, n-butoxy, isobutoxy, s-butyl, n-pentyl group and the like.

Examples of the halogen atom include a fluorine atom, a chlorine atom, a bromine atom and the like.

Examples of the haloalkyl group having 1–5 carbon atoms include a chloromethyl group, a fluoromethyl group, a trifluoromethyl group and the like.

Examples of the alkoxyalkyl group having 2–4 carbon atoms include a methoxymethyl group and the like.

Specific examples of the optionally substituted aralkyl group include a benzyl group, a 4-chlorobenzyl group, a 4-methylbenzyl group, a 4-methoxybenzyl group, a 4-phenoxybenzyl group, a 2,3,5,6-tetrafluorobenzyl group, a 2,3,5,6-tetrafluoro-4-methylbenzyl group, a 2,3,5,6-tetrafluoro-4-methoxybenzyl group, a 2,3,5,6-tetrafluoro-4-methoxymethylbenzyl group and the like.

Specific examples of the chrysanthemic acid ester (1) include methyl chrysanthemate, ethyl chrysanthemate, isopropyl chrysanthemate, cyclohexyl chrysanthemate, menthyl chrysanthemate, benzyl chrysanthemate, 4-chlorobenzyl chrysanthemate, 2,3,5,6-tetrafluorobenzyl chrysanthemate, 2,3,5,6-tetrafluoro-4-methylbenzyl chrysanthemate, 2,3,5,6-tetrafluoro-4-methoxybenzyl chrysanthemate, 2,3,5,6-tetrafluoro-4-methoxymethylbenzyl chrysanthemate, 4-phenoxybenzyl chrysanthemate, and the like. A (+)-trans isomer, a (−)-transisomer, (+)-cis isomer, (−)-cis isomer, a cis/trans or (+)/(−) mixture of the above-described chrysanthemate are also included in the specific examples.

Examples of the catalyst include tungstic trioxide, tungstic acid and tugstate such as sodium tungstate, potassium tungstate, magnesium tungstate, molybdic trioxide, molybdic acid, and molybdate such as sodium molybdate, potassium molybdate, ammonium molybdate, bis(2,4-acetylacetonato)molybdenum dioxide and the like.

Examples of the alkylrhenium oxide include a ($C_1$–$C_5$) alkylrhenium trioxide such as methylrhenium trioxide, ethylrhenium trioxide, n-propylrhenium trioxide, n-butylrhenium trioxide, n-pentylrhenium trioxide or the like.

Examples of the heteropoly acid comprising a hetero atom selected from a phosphorus, boron or silicone atom and a poly atom selected from tungsten or molybdemun and a salt thereof include phosphotungstic acid, silicotungstic acid, borotungstic acid, phosphomolybdic acid, silicomolybdic acid, boromolybdic acid and a salt thereof with lithium, sodium, potassium, magnesium or calcium.

The catalysts described above may be an anhydrate or a hydrate.

An amount of the catalyst to be used is usually 0.001–0.95 mole per mol of the chrysanthemic acid ester (2).

Hydrogen peroxide is usually used as an aqueous hydrogen peroxide solution or a solution of hydrogen peroxide in an organic solvent. The concentration of hydrogen peroxide in an aqueous solution or in an organic solvent is not particularly limited but it is usually 1 to 60% by weight in view of production efficiency of the process. A commercially available aqueous hydrogen peroxide solution is usually used as it is or the concentration of the aqueous solution may be optionally adjusted, for example, by dilution, concentration or the like.

The solution of hydrogen peroxide in an organic solvent can be prepared by extracting an aqueous hydrogen peroxide solution with an organic solvent. Alternatively it may be prepared by removing water from a mixture of an aqueous hydrogen peroxide solution and an organic solvent. Said removal of water can be made by azeotropic distillation of the aqueous hydrogen peroxide solution with an organic solvent that forms an azeotrope with water or dehydration with a dehydrating agent.

An amount of hydrogen peroxide to be used is usually 1 mole or more per mol of the chrysanthemic acid ester (2) and the upper limit thereof is not particularly limited and it is usually 50 moles or less from an economical viewpoint.

For example, the reaction of 3,3-dimethyl-2-(2-methyl-1-propenyl)cyclopropanecarboxylic acid ester (2) with hydrogen peroxide may be conducted in a water-immiscible organic solvent by using dehydrated organic solution of hydrogen peroxide or conducted by using aqueous hydrogen peroxide in a water-miscible organic solvent. Alternatively it may be conducted in water or in a mixture of water and water-immiscible organic solvent in the presence of a phase transfer catalyst such as quaternary ammonium salt or the like. The water derived from aqueous hydrogen peroxide added to the reaction may be removed during the reaction with dehydrating agent or azeotropically.

Examples of the water-immiscible organic solvent include a halogenated hydrocarbon solvent such as carbon tetrachloride, chloroform, dichloroethane, chlorobenzene, o-dichlorobenzene, m-dichlorobenzene and the like, an aromatic hydrocarbon solvent such as benzene, toluene, nitrobenzene and the like, an ether solvent such as diethyl ether, methyl tert-butyl ether, tetrahydrofuran, dioxane and the like, and an ester solvent such as ethyl acetate and the like.

Examples of the water-miscible organic solvent include an alcohol solvent such as methanol, ethanol, tert-butanol and the like, and an alkylnitrile solvent such as acetonitrile, propionitrile and the like.

An amount of the water solvent or the organic solvent is not particularly limited but it is usually 100 parts by weight or less per 1 part by weight of chrysanthemic acid ester (2).

Examples of the quaternary ammonium salt include a quaternary ammonium hydrogen sulfate salt such as n-tetrabutylammonium hydrogen sulfate, n-tetrahexylammonium hydrogen sulfate, methyltricetylammonium hydrogen sulfate or the like. An amount thereof to be used is usually 0.001–1 mole per mol of chrysanthemic acid ester (2).

Examples of the dehydrating agent include anhydrous magnesium sulfate, anhydrous sodium sulfate and the like. An amount thereof to be used is not particularly limited and such an amount of a dehydrating agent that can remove water in the reaction system is usually used.

Tungstate (tungstic acid salts) or molybdate (molybdic acid salts) as described above are preferably used together with a mineral acid so as to enhance the catalytic activity of the same by acidifying the reaction mixture.

Examples of the mineral acid include hydrochloric acid, sulfuric acid, phosphoric acid, or boric acid.

An amount of the mineral acid to be used is usually 1 mole or more per mol of the mineral acid.

The alkylrhenium oxide or molybdic oxide is usually used in a dehydrated condition using an organic solvent and an organic solvent solution of hydrogen peroxide. Alternatively the catalyst may be used, preferably in the presence of a dehydrating agent together with aqueous hydrogen peroxide so as to remove water contained in the reaction mixture.

In this reaction, chrysanthemic acid ester (2), hydrogen peroxide, a catalyst and, if necessary, said water-miscible or water immiscible organic solvent may be mixed and the order of mixing is not particularly limited. The reaction is usually conducted at a temperature of from 0 to 200° C., preferably at 0 to 80° C.

A boron compound may be further added to the present reaction process to help the reaction progress.

Examples of the boron compound include a boric anhydride, a metaboric acid, an orthoboric acid, and an alkali metal salt and an alkaline earth metal salt thereof. An amount thereof to be used is no particularly limited and is usually 1 mole or less per mol of the chrysanthemic acid ester (2).

The progress of the reaction can be monitored by the conventional analyzing means such as gas chromatography, thin layer chromatography, NMR, IR and the like.

After completion of the reaction, the reaction mixture may be filtered to remove insolubles, if necessary.

3,3-dimethyl-2-formylcyclopropanecarboxylic ester of formula (2) can be obtained by, for example, concentrating the reaction mixture, alternatively, it may be extracted with water-immiscible organic solvent after addition of water to a reaction mixture and concentrated to give the desired compound, which may be further purified by such a means as distillation, column chromatography and the like, if necessary.

Examples of the water-immiscible organic solvent include an aliphatic hydrocarbon solvent such as hexane, heptane or the like, an aromatic hydrocarbon solvent such as toluene, xylene or the like, a halogenated hydrocarbon solvent such as dichloromethane, chloroform, chlorobenzene or the like. An amount thereof to be used is not particularly limited.

Specific examples of the 3,3-dimethyl-2-formylcyclopropanecarboxylic acid ester of formula (1) include
methyl 3,3-dimethyl-2-formylcyclopropane-carboxylate,
ethyl 3,3-dimethyl-2-formylcyclopropanecarboxylate,
isopropyl 3,3-dimethyl-2-formylcyclopropane-carboxylate,
cyclohexyl 3,3-dimethyl-2-formylcyclopropane-carboxylate,
menthyl 3,3-dimethyl-2-formylcyclopropane-carboxylate,
benzyl 3,3-dimethyl-2-formylcyclopropane-carboxylate,
4-chlorobenzyl 3,3-dimethyl-2-formylcyclopropane-carboxylate,
2,3,5,6-tetrafluorobenzyl 3,3-dimethyl-2-formyl-cyclopropanecarboxylate,
2,3,5,6-tetrafluoro-4-methylbenzyl 3,3-dimethyl-2-formylcyclopropanecarboxylate,
2,3,5,6-tetrafluoro-4-methoxybenzyl 3,3-dimethyl-2-formylcyclopropanecarboxylate,
2,3,5,6-tetrafluoro-4-methoxymethylbenzyl 3,3-dimethyl-2-formylcyclopropanecarboxylate, and
4-phenoxybenzyl 3,3-dimethyl-2-formylcyclopropane-carboxylate, and the like. Specific examples of 3,3-dimethyl-2-formylcyclopropanecarboxylic acid ester of formula (1) further include (+)-trans, (+)-cis, (−)-trans, (−)-cis-isomer or a mixture thereof.

EXAMPLES

The present invention will be explained in more detail by way of Examples below but is not limited to them. The yield of 3,3-dimethyl-2-formylcyclopropanecarboxylic esters was calculated by the gas chromatography analysis.

Example 1

543 mg of tungstic acid (monohydrate) and 3 g of water were added to a 50 ml flask. 3 g of 60% hydrogen peroxide were added thereto in 5 min and kept at 60° C. under stirring for 1 hour. After being cooled to 30° C., 15 g of tert-butanol and 5.3 g of anhydrous magnesium sulfate were added thereto and stirred for 12 hrs. The resulting mixture was cooled to 15° C. and then a mixed solution of 10 g of tert-butanol and 4 g of methyl trans-3,3-dimethyl-2-(2-methyl-1-propenyl)-cyclopropane-carboxylate was added thereto over 20 min and kept at 15° C. for 24 hours under stirring to obtain a reaction solution containing methyl trans-3,3-dimethyl-2-formylcyclopropanecarboxylate.
Yield: 55.5% (Gas-Chromatography analysis using Internal Standard)

Example 2

27 mg of methylrhenium trioxide and 600 mg of 30% aqueous hydrogen peroxide were added to a 50 ml flask. and kept at 60° C. under stirring for 1 hour. After being cooled to 25° C., 1.5 g of tert-butanol and 530 mg of anhydrous magnesium sulfate were added thereto and then a mixed solution of 1.5 g of tert-butanol and 400 mg of methyl trans-3,3-dimethyl-2-(2-methyl-1-propenyl)-cyclopropane-carboxylate was added thereto over 20 min. and kept at 25° C. for 24 hours under stirring to obtain a reaction solution containing methyl trans-3,3-dimethyl-2-formylcyclo-propane-carboxylate. Yield: 21.6% (Gas-Chromatography analysis using Internal Standard)

Example 3

55 mg of tungstic acid (monohydrate), 6 mg of 85% phosphoric acid and 600 mg of 30% hydrogen peroxide were added to a 50 ml flask, and kept at 60° C. under stirring for 1 hour. After being cooled to 25° C., 1.5 g of tert-butanol and 530 mg of anhydrous magnesium sulfate were added thereto and a solution of 1.5 g of tert-butanol and 400 mg of methyl trans-3,3-dimethyl-2-(2-methyl-1-propenyl)-cyclopropanecarboxylate was added thereto over 20 min and kept at 15° C. for 14 hours under stirring to obtain a reaction solution containing methyl trans-3,3-dimethyl-2-formylcyclopropanecarboxylate.
Yield: 44.6% (Gas-Chromatography analysis using Internal Standard)

Example 4

72 mg of sodium tungstate (trihydrate), 22 mg g of concentrated sulfuric acid and 600 mg of 30% aqueous hydrogen peroxide were added to a 50 ml flask, and kept at 60° C. under stirring for 1 hour. After being cooled to 25° C., 1.5 g of tert-butanol and 530 mg of anhydrous magnesium sulfate were added thereto and then a mixed solution of 1.5 g of tert-butanol and 400 mg of methyl trans-3,3-dimethyl-2-(2-methyl-1-propenyl)-cyclopropane-carboxylate was added thereto over 20 min. and kept at 25° C. for 24 hours under stirring to obtain a reaction solution containing methyl trans-3,3-dimethyl-2-formylcyclopropanecarboxylate.
Yield: 40.9% (Gas-Chromatography analysis using Internal Standard)

Example 5

21 mg of molybdenum trioxide and 600 mg of 30% aqueous hydrogen peroxide were added to a 50 ml flask and kept at 60° C. under stirring for 1 hour. After being cooled to 25° C., 1.5 g of tert-butanol and 530 mg of anhydrous magnesium sulfate were added thereto. After the resulting mixture was warmed to 60° C., a mixed solution of 1.5 g of tert-butanol and 400 mg of methyl trans-3,3-dimethyl-2-(2-methyl-1-propenyl)-cyclopropanecarboxylate was added thereto over 20 min. and kept at 60° C. for 6 hours under stirring to obtain a reaction solution containing methyl trans-3,3-dimethyl-2-formylcyclopropane-carboxylate.
Yield: 18% (Gas-Chromatography analysis using Internal Standard)

Example 6

55 mg of tungstic acid (monohydrate), 12 mg of boric anhydride and 600 mg of 30% hydrogen peroxide were added to a 50 ml flask and kept at 40° C. under stirring for 1 hour. After being cooled to 25° C., 1.5 g of tert-butanol, 530 mg of anhydrous magnesium sulfate and a mixed solution of were added thereto and stirred for 5 min. Then 1.5 g of tert-butanol and 400 mg of methyl trans-3,3-dimethyl-2-(2-methyl-1-propenyl)cyclopropanecarboxylate was added thereto over 20 min and kept at 25° C. for 24 hours under stirring to obtain a reaction solution containing methyl trans-3,3-dimethyl-2-formylcyclopropanecarboxylate.
Yield: 41.3% (Gas-Chromatography analysis using Internal Standard)

Example 7

50 mg of 12 tungsto(VI)phoshoric acid (n-hydrate) and 600 mg of 30% hydrogen peroxide were added to a 50 ml flask and kept at 40° C. under stirring for 1 hour. After being cooled to 25° C., 1.5 g of tert-butanol and 530 mg of anhydrous magnesium sulfate were added thereto and stirred for 5 min. Then 1.5 g of tert-butanol and 400 mg of methyl trans-3,3-dimethyl-2-(2-methyl-1-propenyl)cyclopropane-carboxylate was added thereto over 20 min and kept at 25° C. for 24 hours under stirring to obtain a reaction solution containing methyl trans-3,3-dimethyl-2-formylcyclopropanecarboxylate.
Yield: 45.8% (Gas-Chromatography analysis using Internal Standard)

Example 8

5 g of tert-butanol, 1.0 g of 30% by weight aqueous hydrogen peroxide, 2 g of anhydrous magnesium sulfate and 20 mg of tungsten trioxide were placed in a 50 ml flask, an inner temperature was raised to 60° C., and a mixed solution of 100 mg of racemic trans-3,3-dimethyl-2-(2-methyl-1-propenyl)cyclopropanecarboxylate in 1 g of tert-butanol was added dropwise over 10 minutes. Thereafter, the mixture was stirred at an inner temperature of 60° C. for 2 hours and held to obtain the reaction mixture containing racemic trans-3,3-dimethyl-2-formylcyclopropanecarboxylic acid ester. 33% (Areal percentage of the obtained ester product in the gas chromatography analysis chart of the mixture, hereinafter referred to as "GC Area %").

Example 9

5 g of methyl tert-butyl ether, 1.0 g of 30 wt % aqueous hydrogen peroxide, 2 g of anhydrous magnesium sulfate and 10 mg of methylrhenium trioxide were placed in a 50 ml flask, and the temperature was raised to 50° C., and a solution of 100 mg of racemic ethyl trans-3,3-dimethyl-2-(2-methyl-1-propenyl)cyclopropane-carboxylate in 1 g of methyl tert-butyl ether was added dropwise thereto over 10 min. Thereafter, the mixture was stirred at an inner temperature of 50° C. for 2 hours and held to obtain the reaction mixture containing racemic ethyl trans-3,3-dimethyl-2-formylcyclopropane-carboxylate. 23% (GC Area %)

Example 10

1.0 g of 30% aqueous hydrogen peroxide, 10 mg of tungsten oxide, 10 mg of n-tetrabutylammonium hydrogen sulfate and 100 mg of racemic ethyl trans-3,3-dimethyl-2-(2-methyl-1-propenyl)-cyclopropanecarboxylate were placed in a 50 ml flask, the mixture was stirred at 60° C. for 2 hours and held to obtain the reaction mixture containing racemic ethyl trans-3,3-dimethyl-2-formyl-cyclopropane-carboxylate. 27% (GC Area %)

Example 11

1.0 g of 30% aqueous hydrogen peroxide, 10 mg of sodium tungstate, 10 mg of methyltricetylammonium hydrogen sulfate and 100 mg of racemic ethyl trans-3,3-dimethyl-2-(2-methyl-1-propenyl)-cyclopropanecarboxylate were placed in a 50 ml flask, the mixture was stirred at an inner temperature of 60° C. for 2 hours and held to obtain the reaction mixture containing racemic ethyl trans-3,3-dimethyl-2-formylcyclopropanecarboxylate. 27% (GC Area %)

What is claimed is:
1. A process for producing 3,3-dimethyl-2-formylcyclopropanecarboxylic ester of formula (1):

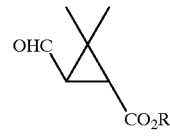

(1)

wherein R represents an alkyl group, a cycloalkyl group or an optionally substituted aralkyl group,
which comprises reacting chrysanthemic acid ester of formula (2):

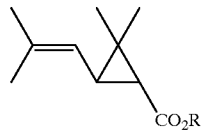

(2)

wherein R represents the same meaning as that described above, with hydrogen peroxide in the presence of at least one catalyst selected from the group consisting of tungstic oxide, tungstic acid, tungstate, molybdic oxide and molybdate.

2. A process according to claim 1, wherein R represents
a linear or branched lower alkyl group having 1–5 carbon atoms,
a cycloalkyl group having 3–10 carbon atoms,
a phenyl- or naphthyl-substituted (C1–C5)alkyl group, of which phenyl group or naphthyl group may be substituted with at least one group selected from the linear or branched lower alkyl group having 1–5 carbon, a lower alkoxy group having 1–5 carbon atoms, a halogen atom, a haloalkyl group having 1–5 carbon atoms, a phenoxy group, and an alkoxyalkyl group having 2–4 carbon atoms.

3. A process according to claim 1 or 2, wherein said one catalyst is tungstic trioxide, tungstic acid, sodium tungstate, potassium tungstate, magnesium tungstate, molybdic trioxide, molybdic acid, sodium molybdate, potassium molybdate, ammonium molybdate or bis(2,4-acetylacetonato) molybdemun.

* * * * *